United States Patent [19]

Sheets et al.

[11] Patent Number: 4,787,902
[45] Date of Patent: Nov. 29, 1988

[54] MULTI-POSITIONABLE INTRAOCULAR LENS

[76] Inventors: John H. Sheets, 104 Chukar Run, Odessa, Tex. 79763; Roger E. Lagerquist, 6826 Pasado Rd.; Bruce A. Christie, 40 San Rossano Dr., both of, Goleta, Calif. 93117

[21] Appl. No.: 364,280

[22] Filed: Apr. 1, 1982

[51] Int. Cl.⁴ .............................................. A61F 2/16
[52] U.S. Cl. .................................................. 623/6
[58] Field of Search .......................................... 3/13, 1

[56] References Cited

U.S. PATENT DOCUMENTS 4,174,543 11/1979 Kelman ..................... 3/13
4,249,271 2/1981 Poler ......................... 3/13

FOREIGN PATENT DOCUMENTS 0032835 7/1981 European Pat. Off. ............... 3/13

OTHER PUBLICATIONS

New Implens 30 Intraocular Lens (Sheet Design), Advertisement Brochure, McGhan/3M (4 pages), published Mar. 1980.
The Linstrom Centrex Style 20 Posterior Chamber Lens by Surgidev (Advertisement), 4 pages, 1981.

Primary Examiner—Ronald L. Frinks
Attorney, Agent, or Firm—Mason, Fenwick & Lawrence

[57] ABSTRACT

An intraocular lens for positioning in either the anterior or posterior chambers of the eye includes a lens body having first and second support members extending from the lens body for engaging adjacent portions of the anterior or posterior chamber of the eye, each comprising a resilient spring-like asymmetric support loop extending outwardly from the periphery of the lens body and having first and second parallel end portions embedded in chordal bores in the periphery of the lens body; first and second sloped leg portions of different lengths extend outwardly from the end portions and a transverse portion extends transversely from outer ends of the first and second leg portions and includes contact foot portions on each end which are separated by an inwardly extending arcuate connector portion.

7 Claims, 2 Drawing Sheets

PRIOR ART ns suitable for use as an artificial lens implant in either the anterior or posterior chamber of the human eye. Particularly, this invention relates to an intraocular lens having at least one asymmetric resilient spring-like support loop which contains sloped portions which provide the lens with a vault and outer contact portion for holding the lens in place in the eye.

MULTI-POSITIONABLE INTRAOCULAR LENS

BACKGROUND OF THE INVENTION

This invention relates to an intraocular lens suitable for use as an artificial lens implant in either the anterior or posterior chamber of the human eye. Particularly, this invention relates to an intraocular lens having at least one asymmetric resilient spring-like support loop which contains sloped portions which provide the lens with a vault and outer contact portion for holding the lens in place in the eye.

Intraocular lens implantation after cataract surgery has come into common usage because of the improved vision obtained thereby over the alternatives of contact lenses or spectacles. Intraocular lenses have been implanted in both the posterior as well as the anterior chambers of the eye. In general format, an intraocular lens consists of a lens body and a plurality of support members usually projecting from different sides of the lens body for use in supporting the lens in position in the eye. Within the basic format, however, several different designs of intraocular lenses are currently available. In most of these, the position fixation elements or support means are in the form of rigid loops, arms, plates, legs, and the like, such as exemplified by the rigid loops 12 and 13 in Jensen U.S. Pat. No. 4,110,848 and by the rigid plates 12 and 13 of Kelman U.S. Pat. No. 4,092,743. Both the Jensen and the Kelman patents disclose rigid loops or plates which extend through the iris. Prongs extending through the iris are disclosed as fixation means in the Flom U.S. Pat. No. 3,866,249. Jensen et al U.S. Pat. No. 3,994,027 and Payman et al U.S. Pat. No. 4,073,015 both disclose rigid support loops engaging the anterior capsule wall.

A recent more flexible posterior chamber lens is disclosed by Shearing U.S. Pat. No. 4,159,546 in which J-shaped elastic support members extend outwardly from opposite peripheral edges of the lens to engage the ciliary body, or possibly the lens capsule, to support the lens in position.

It has also been proposed by Grinder, in Ser. No. 113,682, to employ flexible capsule engaging support loops of a shape similar to element 12 of the Kelman U.S. Pat. No. 4,092,743 with two of such loops extending from opposite sides of the lens body. Additionally, Sheets, in U.S. Ser. No. 071,375, employs flexible support loops for engagement with the lens capsule.

Furthermore, it is known to fashion the support members of the lens so that they have sloped or inclined portions which result in the portions of the support members which are to contact the eye being non-planar with the lens body. Such lenses are said to be "vaulted" and are disclosed in, for example, U.S. Pat. Nos. 2,834,023; 4,092,743; 4,110,848 and 4,134,161.

FIGS. 6 and 7 illustrate prior art lenses having support loops which contain sloped or vaulted portions. Referring to FIG. 6, an elevational view of a vaulted two-loop lens 81 is shown. The lens of FIG. 6 includes a lens body 82 which has a convex anterior surface and a flat posterior surface, and identical symmetric support loops 86 and 87 made of a polymeric material. Loops 86 and 87 have end portions 89 and 95 attached to lens body 82 and columnar leg portions 90 and 94 which extend from end portions 89 and 95 respectively. Loops 86 and 87 also have transverse portion 91 which extends transversely between leg portions 90 and 94 and contains a first contact portion 92 and second contact portion 93. Loops 86 and 87 contain sloped portions lying between imaginary lines G and H which are inclined somewhat posteriorly to lens body 82. These sloped portions are inclined such that transverse portion 91 lies in a plane parallel to the posterior of the lens body 82. Imaginary lines G and H are parallel to an imaginary line I which is perpendicular to both columnar leg portions 90 and 94 and intersects and is perpendicular to the geometric axis 88 of the lens body 82. The lens illustrated by FIG. 6 is commercially available as the "Leiske [R] Physioflex [R] Style 10 Anterior Chamber Lens" from Surgidev Corporation.

Referring to FIG. 7, an elevational view of another vaulted loop lens of the prior art is shown. The lens 101 includes a lens body 102 which is identical to the lens body 82, and identical support loops 106 and 107 which are made of polymeric material. The loops 106 and 107 have portions 109 and 115 attached to the lens body and columnar leg portions 110 and 114 which extend from end portions 109 and 115 respectively. Connecting legs 110 and 114 is a transverse portion comprising a first contact foot portion 111 and a second contact foot portion 113 with each foot portion being of arcuate configuration having a center of curvature between it and the lens body 102, as is apparent from an inspection of FIG. 7. Contact portions 111 and 113 are connected by an inwardly extending oppositely curved arcuate connector portion 112 which has a center of curvature positioned outwardly from itself with respect to the lens body 102.

Loops 106 and 107 also contain sloped portions lying between imaginary lines J and K, which are inclined somewhat posteriorly to lens body 102. These sloped portions are inclined such that portions 111, 112, and 113 lie in a plane which is substantially parallel to the posterior surface of the lens body 102. Imaginary lines J and K are parallel to an imaginary line L which is perpendicular to the columnar leg portions 110 and 114 and intersects the geometric axis 108 of the lens body 102. The lens illustrated by FIG. 7 is commercially available as the "Anterior Chamber Liteflex [R] Style 70 Intraocular Lens" from McGhan/3M.

Notwithstanding the great strides made in lens implantation, as evidenced by the thousands of successful lens implantations, complications in individual cases continue to arise in a small percentage of the cases. For example, the lenses of the prior art are relatively unstable and are easily mispositioned which may cause them to come in contact with the cornea or iris, thereby causing cell death or erosion of these parts of the eye. Improper sizing and excessive weight of the lens and support elements also cause subsequent mispositioning of the lens in some instances. Additionally, the use of sutures in other similar connectors engaging viable portions of the eye may cause cell death or erosion of these parts of the eye.

This invention provides an improved and more stable intraocular lens for positioning in either the anterior or posterior chamber of the eye. The lens of this invention is easy to implant and has stability without suturing.

SUMMARY OF THE INVENTION

The lens of the present invention comprises a lens body having first and second support members extending from the lens body for engaging adjacent portions of the anterior or posterior chamber of the eye. At least one of the support members comprises a resilient spring-like asymmetric support loop extending outwardly from the periphery of the lens body with the support loop having first and second parallel end portions attached to the lens body at first and second attachment locations extending chordally with respect to the lens body. First and second leg portions extend from the first and second end portions respectively, each of said leg portions being sloped relative to a plane perpendicular to the axis of the lens body. A transverse portion has opposite sides respectively unitarily connected to the outer ends of the first and second legs and also includes one or more outer contact foot portions dimensioned and shaped to engage adjacent portions of the anterior or posterior chambers of the eye with an outward radial force when positioned therein so that at least one of the outer contact portions is deflected inwardly from the normal relaxed position by the adjacent portion of the eye to provide support for the lens body. The transverse portion is positioned in a plane which is spaced apart from but substantially parallel to the plane of the lens body. The support members extend outwardly in a symmetrical manner from generally opposite sides of the periphery of the lens body. The sloped portions of the leg portions provide the lens with a vaulted configuration.

Due to the particular construction of the asymmetric support loop of the lens, that is, the inclusion of first and second leg portions having sloped portions, the lens of the present invention is highly flexible and highly stable, with a reduced tendency to become mispositioned when implanted in the eye. The lens is designed for easy and essentially automatic and accurate positioning within either the anterior or posterior chambers of the eye, preferably within the posterior. The lens is vertically, horizontally, and rotationally secured by the spring action of the support loops in contact with the adjacent portions of the eye. There is normally no need for suturing of the support means to any portion of the eye, and when the lens is placed in the eye, there is ordinarily an absence of contact with the cornea and iris. Thus, there is an attendant absence of problems which can be caused by lenses which come in contact with these portions of the eye.

BRIEF DESCRIPTION OF THE DRAWINGS

The invention will now be described in more detail with reference to the drawings in which like reference numerals are used for the same parts as shown in different Figures.

Referring now to FIGS. 1 and 2, the lens 1 comprises a lens body 2 having cylindrical peripheral surface 3, a planar surface 4, and a spherical surface 5. The lens body 2 is normally four to six millimeters in diameter and is made by molding or lathing optical polymeric material such as polymethyl methacrylate. The spherical surface 5 is of a desired curvature to give the required optical characteristics for the particular patient in which the lens is to be implanted. Apertures 13 and 14 are provided in the lens for permitting receipt of the ends of an instrument or tool for holding and positioning the lens during and after insertion in the eye.

The lens body 2 is held in place in the eye by means of two identical support loops 6 and 7. The support loops are made of a resilient spring-like material such as polypropylene. However, other materials having similar resiliency characteristics can be used if they are inert and substantially nonreactive in the human body. Preferably, the loops are formed so as to have a circular cross-section of about 0.10 to 0.30 mm in diameter, preferably about 0.15 mm in diameter.

Figure 1:
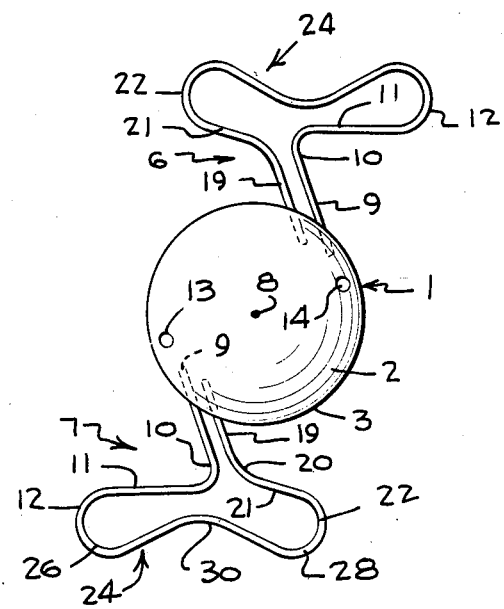
FIG. 1 is a front elevation view of the preferred embodiment of the invention.
Figure 2:
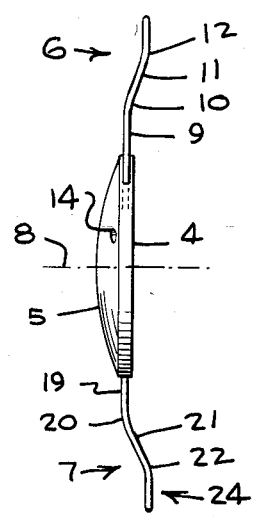
FIG. 2 is a side elevation view of the preferred embodiment.

The support loops 6 and 7 have identical asymmetric foot-like configurations with the ankle portion of each foot being attached to the lens body 2. Loops 6 and 7 are generally symmetrical with the optical as well as the geometric axis 8 of the lens body 2. In the relaxed condition of the lens 1, as shown in FIG. 1, the outermost portions of the respective loops are preferably about 14 millimeters apart if the lens is to be placed in the ciliary sulcus. If the lens is to be positioned in the capsular bag, it is preferred that the loops be about 13 mm apart.

Each support loop contains a first linear end portion 9 embeddedly attached in a chordal bore in the lens body 2 and extending outwardly to a transition portion 10 joining the end portion 9 to a first sloped leg portion 11 which extends to a first outer transition portion 12. A second linear end portion 19 is similarly embedded in a chordal bore in the lens body and extends outwardly to a second inner transition portion 20 joining the second end portion 19 to a second sloped leg portion 21 which extends outwardly to a second outer transition portion 22. The linear end portions 9 and 19 are in a plane perpendicular to the axis 8 of the lens. A transverse portion, generally designated 24, extends between the first outer transition portion 12 and the second outer transition portion 22 and is dimensioned and shaped to engage portions of the eye in which the lens is positioned as will be discussed in detail hereinafter. It should be observed that the transverse portion 24 is positioned in a plane perpendicular to the geometric axis 8 of the lens body 2 and is parallel to a second plane in which the first linear end portion 9 and the second linear end portion 19 are positioned. The leg portions 11 and 21 are canted relative to the axis 8 so as to provide a "vaulted" arrangement.

The transverse portion 24 includes a first arcuately curved contact foot portion 26 and a second arcuately curved contact foot portion 28 with the contact foot portions being in substantially parallel orientation and also being connected by an inwardly extending arcuate connector portion 30. It will be observed that the contact foot portions 26 and 28 press outwardly for contact with the surfaces of the eye in which the lens is positioned. It should be noted that the first sloped leg portion 11 of each support loop is longer than the second sloped leg portion 21, and the contact foot portion 26 consequently is spaced outwardly a greater distance relative to the axis of the lens so as to provide improved resistance to torsional movement of the lens. Also, the first sloped leg 11 is substantially longer than the second sloped leg 21.

Figure 3:
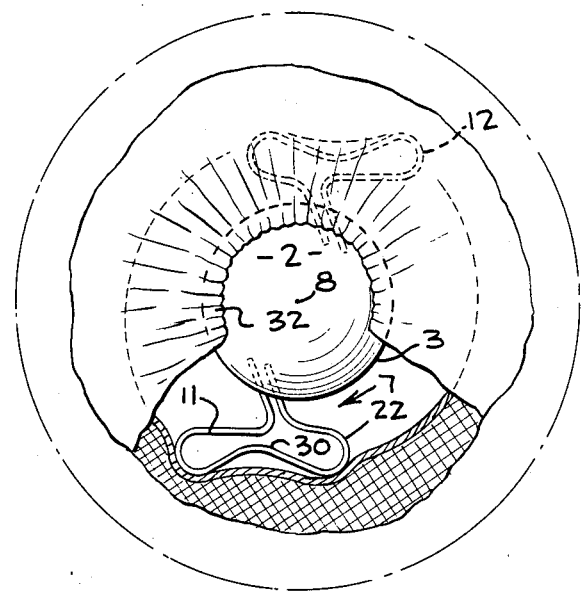
FIG. 3 is a front elevation view of the preferred embodiment of the invention as implanted in the posterior chamber of the eye with portions of the iris removed for clarity of illustration.
Figure 4:
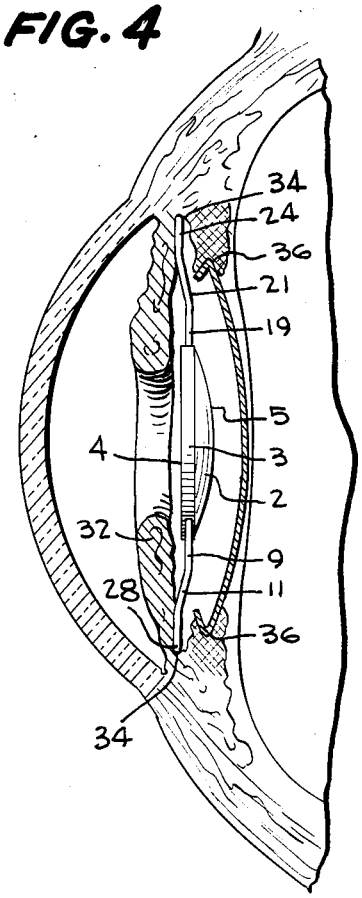
FIG. 4 is a bisecting sectional view of the eye of FIG. 3 with the lens in the posterior implanted position.

FIGS. 3 and 4 illustrate the manner in which the lens is positionable in the posterior chamber of the eye adjacent the iris 32 but positioned so that the lens body 2 does not contact the iris. The positioning of the lens body is effected by virtue of the sloped leg portions 11 and 21 which position the lens body posteriorly of the iris as clearly shown in FIG. 4. It will be observed that the lens body 2 is positioned with its planar surface 4 facing forwardly, an arrangement that is not normally employed with lens implants; but which provides the same optical effect as the normal orientation in which the spherical surface 5 faces forwardly. The lens as shown in FIG. 4 has been positioned in the posterior chamber of the eye after the natural lens has been removed from the lens capsule by normal extracapsular cataract removal. It will be observed that the transverse portion 24 of each of the support loops 6 and 7 is positioned in contact with the ciliary sulcus 34 of the eye. The resilient nature of the support loops results in their forcefully engaging the ciliary sulcus so as to hold the lens in the position shown in FIG. 4. Moreover, it should be understood that it would also be possible to position a lens of the inventive type in the equatorial region 36 of the lens capsule although it would be necessary to employ a somewhat smaller lens and associated support loops due to the reduced diameter of the equatorial region 36 of the capsule as compared to the diameter of the ciliary sulcus 34.

Figure 5:
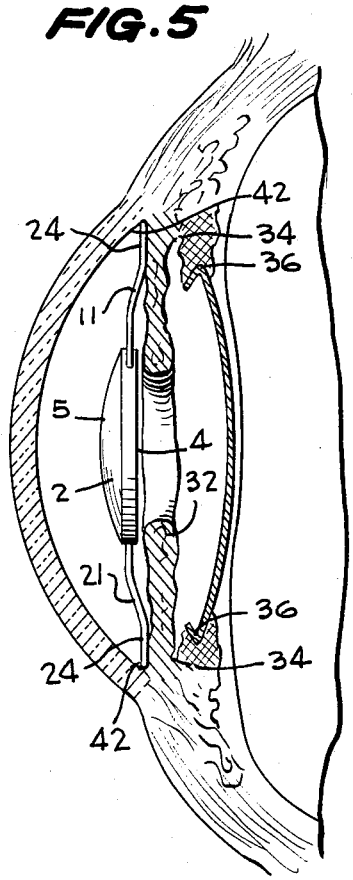
FIG. 5 is a sectional view of the eye with the preferred embodiment of the lens of the invention in the anterior implanted position.
Figure 6:
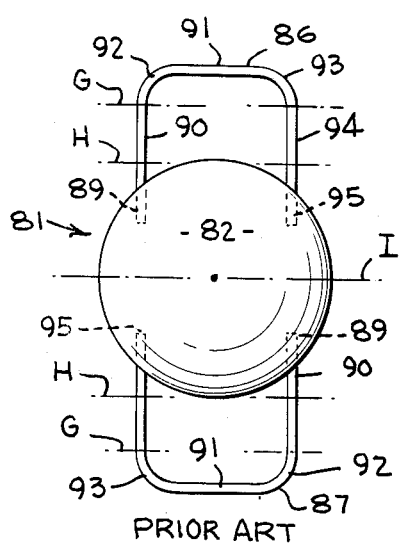
FIGS. 6 and 7 are front elevation views of prior art lenses.
Figure 7:
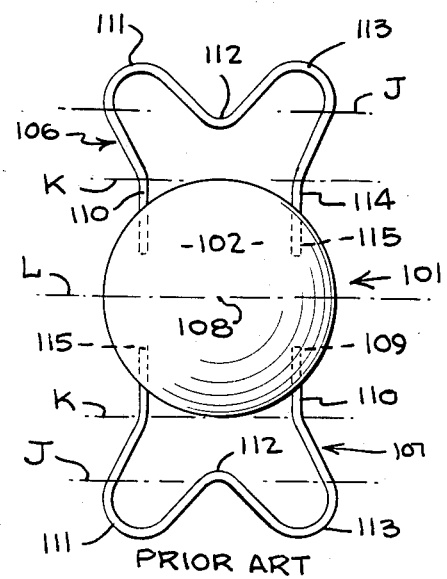

Alternatively, the lens can be positioned in the anterior chamber of the eye as shown in FIG. 5. As thus positioned, the transverse portions 24 of the support loops 6 and 7 are positioned adjacent the scleral spur 72 with the sloped leg portions 11 and 21 serving to hold the lens body 2 in a sufficiently forward position as to preclude contact of the lens body with the iris 32.

The asymmetric configuration of the support loops results in improved stability of the lens when positioned in either chamber of the eye.

Numerous modifications of the preferred embodiment not departing from the spirit of the invention will undoubtedly occur to those of skill in the art. It should therefore be understood that the scope of the invention is to be limited solely by the appended claims.

We claim:

1. An intraocular lens assembly dimensioned and shaped for positioning in either the anterior chamber or posterior chamber of the eye comprising a lens body; first and second support members extending form the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second sloped leg portions respectively extending outwardly from said first and second end portions and a transverse portion extending generally transversely relative to said first and second leg portions and with opposite sides being respectively unitarily connected to outer ends of said first and second leg portions and having at least one outer contact portion dimensioned and shaped to engage adjacent portions of the anterior or posterior chambers of the eye with an outward radial force when positioned therein so that said outer contact portion is deflected inwardly form the normal relaxed position by the adjacent portion of the eye to provide support for said lens body, said transverse portion lying in a plane which is spaced apart from but substantially parallel to the plane of said lens body, wherein said first and second end portions are axially parallel at their inner extent and are received in chordal bores provided in the lens body, and wherein said chordal bores are both on one side of a diameter of the lens body with respect to which said bores are parallel.

2. An intraocular lens assembly dimensioned and shaped for positioning in either the anterior chamber or posterior chamber of the eye comprising a lens body; first and second support members extending from the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second sloped leg portions respectively extending outwardly from said first and second end portions and a transverse portion extending generally transversely relative to said first and second portions and with opposite sides being respectively unitarily connected to outer end of said first and second leg portions and having at least one outer contact portion dimensioned and shaped to engage adjacent portions of the anterior or posterior chambers of the eye with an outward radial force when positioned therein so that said outer contact portion is deflected inwardly from the normal relaxed position by the adjacent portion of the eye to provide support for said lens body, said transverse portion lying in a plane which is spaced apart from but substantially parallel to the plane of said lens body, wherein said transverse portion comprises first and second contact foot portions which protrude outwardly at first and second ends respectively of said transverse portion and an arcuate connector portion extending inwardly between said first and second contact foot portions, wherein said first and second end portions are axially parallel at their inner extent and are received in chordal bores provided in the lens body, and wherein said chordal bores are both on one side of a diameter of the lens body with respect to which said bores are parallel.

3. An intraocular lens assembly dimensioned and shaped for positioning in either the anterior chamber or posterior chamber of the eye comprising a lens body; first and second support members extending from the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second sloped leg portions respectively extending outwardly from said first and second end portions and a transverse portion extending generally transversely relative to said first and second leg portions and with opposite sides being respectively unitarily connected to outer ends of said first and second leg portions and having at least one outer contact portion dimensioned and shaped to engage adjacent portions of the anterior or posterior chambers of the with an outward radial force when positioned therein so that said outer contact portion is deflected inwardly from the normal relaxed position by the adjacent portion of the eye to provide support for said lens body, said transverse portion lying in a plane which is spaced apart from but substantially parallel to the plane of said lens body, wherein said first sloped leg portion and said second sloped leg portion extend outwardly from said first and second end portions in substantially opposite directions, wherein said first sloped leg portion is substantially longer than said second sloped leg portion, wherein said first and second end portions are axially parallel at their inner extent and are received in chordal bores provided in the lens body, and wherein said chordal bores are both on one side of a diameter of the lens body with respect to which said bores are parallel.

4. An intraocular lens assembly dimensioned and shaped for positioning in either the anterior chamber or posterior chamber of the eye comprising a lens body; first and second support members extending from the lens body for engaging adjacent portions of the anterior or posterior chamber of the eye, at least one of said support members comprising a resilient spring-like asymmetric support loop extending outwardly from the periphery of said lens body, said support loop having first and second end portions attached to the lens body at first and second attachment locations, first and second sloped leg portions respectively extending outwardly from said first and second end portions and a transverse portion extending generally transversely relative to said first and second leg portions and with opposite sides being respectively unitarily connected to outer ends of said first and second leg portions and having at least one outer contact portion dimensioned and shaped to engage adjacent portions of the anterior or posterior chambers of the eye with an outward radial force when positioned therein so that said outer contact portion is deflected inwardly form the normal relaxed position by the adjacent portion of the eye to provide support for said lens body, said transverse portion lying in a plane which is spaced apart from but substantially parallel to the plane of said lens body, wherein said first and second support members are identical and are symmetrically positioned on opposite sides of said lens body, wherein said first and second end portions of each respective support loop are axially parallel at their inner extent and are received in chordal bores in the lens body, and wherein said chordal bores of each respective support loop are both on one side of a diameter of the lens body with respect to which said bores are parallel.

5. The intraocular lens of claim 4 wherein said transverse portion of each support member comprises first and second contact foot portions which protrude outwardly at first and second ends respectively of said transverse portion and an arcuate connector portion extending inwardly between said first and second contact foot portions.

6. The intraocular lens of claim 5 wherein said first sloped leg portion and said second sloped leg portion of each loop extend outwardly from said first and second end portions in substantially opposite directions.

7. The intraocular lens of claim 6 wherein said first sloped leg portion is substantially longer than said second sloped leg portion of each support loop.

* * * * *